United States Patent
Von Arx et al.

(10) Patent No.: US 8,706,251 B2
(45) Date of Patent: *Apr. 22, 2014

(54) SECURE LONG-RANGE TELEMETRY FOR IMPLANTABLE MEDICAL DEVICE

(75) Inventors: Jeffrey A. Von Arx, Minneapolis, MN (US); Allan T. Koshiol, Lino Lakes, MN (US); Joseph E. Bange, Eagan, MN (US)

(73) Assignee: Cardiac Pacemakers, St. Paul, MN (US)

( * ) Notice: Subject to any disclaimer, the term of this patent is extended or adjusted under 35 U.S.C. 154(b) by 1651 days.

This patent is subject to a terminal disclaimer.

(21) Appl. No.: 11/640,552

(22) Filed: Dec. 18, 2006

(65) Prior Publication Data

US 2007/0118188 A1    May 24, 2007

Related U.S. Application Data

(63) Continuation of application No. 10/601,763, filed on Jun. 23, 2003, now Pat. No. 7,155,290.

(51) Int. Cl.
*A61N 1/372* (2006.01)
(52) U.S. Cl.
CPC .................................. *A61N 1/37252* (2013.01)
USPC .......................................................... 607/60
(58) Field of Classification Search
USPC ..................................................... 607/59–60
See application file for complete search history.

(56) References Cited

U.S. PATENT DOCUMENTS

| | | | |
|---|---|---|---|
| 3,914,586 A | 10/1975 | McIntosh | |
| 4,404,972 A | 9/1983 | Gordon et al. | |
| 4,539,992 A | 9/1985 | Calfee et al. | |
| 4,561,443 A | 12/1985 | Hogrefe et al. | |
| 4,562,841 A | 1/1986 | Brockway et al. | |
| 4,613,937 A | 9/1986 | Batty, Jr. | |
| 5,074,308 A | 12/1991 | Sholder et al. | |
| 5,080,096 A * | 1/1992 | Hooper et al. | 607/30 |
| 5,230,003 A | 7/1993 | Dent et al. | |

(Continued)

FOREIGN PATENT DOCUMENTS

| | | |
|---|---|---|
| JP | 2003-022008 | 1/2003 |
| WO | WO-2005000397 A1 | 1/2005 |

(Continued)

OTHER PUBLICATIONS

"U.S. Appl. No. 10/914,641, Notice of Allowance mailed Oct. 6, 2010", 5 pgs.

(Continued)

*Primary Examiner* — Eric D. Bertram
(74) *Attorney, Agent, or Firm* — Schweman, Lundberg & Woessner, P.A.

(57) ABSTRACT

A method and system for enabling secure communications between an implantable medical device (IMD) and an external device (ED) over a telemetry channel. A telemetry interlock may be implemented which limits any communications between the ED and the IMD over the telemetry channel, where the telemetry interlock is released when the ED transmits an enable command to the IMD via a short-range communications channel requiring physical proximity to the IMD. As either an alternative or addition to the telemetry interlock, a data communications session between the IMD and ED over the telemetry channel may be allowed to occur only after the IMD and ED have been cryptographically authenticated to one other.

20 Claims, 4 Drawing Sheets

(56) References Cited

U.S. PATENT DOCUMENTS

| | | | |
|---|---|---|---|
| 5,404,877 | A | 4/1995 | Nolan et al. |
| 5,456,692 | A | 10/1995 | Smith, Jr. et al. |
| 5,630,835 | A | 5/1997 | Brownlee |
| 5,683,432 | A | 11/1997 | Goedeke et al. |
| 5,725,559 | A | 3/1998 | Alt et al. |
| 5,737,419 | A | 4/1998 | Ganesan |
| 5,807,397 | A | 9/1998 | Barreras |
| 5,843,139 | A | 12/1998 | Goedeke et al. |
| 5,898,397 | A | 4/1999 | Murray |
| 6,028,527 | A | 2/2000 | Soenen et al. |
| 6,044,485 | A | 3/2000 | Dent et al. |
| 6,128,528 | A | 10/2000 | Ericksen et al. |
| 6,169,925 | B1 | 1/2001 | Villaseca et al. |
| 6,336,900 | B1 | 1/2002 | Alleckson et al. |
| 6,385,318 | B1 | 5/2002 | Oishi |
| 6,424,867 | B1 | 7/2002 | Snell et al. |
| 6,434,429 | B1 | 8/2002 | Kraus et al. |
| 6,443,891 | B1 | 9/2002 | Grevious |
| 6,453,198 | B1 | 9/2002 | Torgerson et al. |
| 6,463,329 | B1 | 10/2002 | Goedeke |
| 6,470,215 | B1 | 10/2002 | Kraus et al. |
| 6,562,001 | B2 | 5/2003 | Lebel et al. |
| 6,564,104 | B2 | 5/2003 | Nelson et al. |
| 6,564,105 | B2 | 5/2003 | Starkweather et al. |
| 6,567,793 | B1 | 5/2003 | Hicks et al. |
| 6,574,510 | B2 | 6/2003 | Von Arx et al. |
| 6,600,952 | B1 | 7/2003 | Snell et al. |
| 6,602,191 | B2 | 8/2003 | Quy |
| 6,622,050 | B2 | 9/2003 | Thompson |
| 6,687,546 | B2 | 2/2004 | Lebel et al. |
| 6,889,081 | B2 | 5/2005 | Hsu |
| 6,907,291 | B1 | 6/2005 | Snell et al. |
| 7,155,290 | B2 | 12/2006 | Von et al. |
| 7,228,182 | B2 | 6/2007 | Healy et al. |
| 7,274,642 | B2 | 9/2007 | Sako et al. |
| 7,475,245 | B1 | 1/2009 | Healy et al. |
| 7,818,067 | B2 | 10/2010 | Healy et al. |
| 7,860,574 | B2 | 12/2010 | Von Arx et al. |
| 7,890,180 | B2 | 2/2011 | Quiles |
| 8,041,432 | B2 | 10/2011 | Von Arx et al. |
| 8,046,080 | B2 | 10/2011 | Von Arx et al. |
| 8,494,647 | B2 | 7/2013 | Quiles |
| 8,538,528 | B2 | 9/2013 | Von Arx et al. |
| 2001/0001014 | A1 | 5/2001 | Akins et al. |
| 2001/0019614 | A1 | 9/2001 | Madoukh |
| 2001/0027331 | A1 | 10/2001 | Thompson |
| 2002/0032661 | A1 | 3/2002 | Schuba et al. |
| 2002/0062139 | A1 | 5/2002 | Ding |
| 2002/0115912 | A1 | 8/2002 | Muraki et al. |
| 2002/0120838 | A1 | 8/2002 | Abdulkader |
| 2002/0143372 | A1 | 10/2002 | Snell et al. |
| 2002/0147388 | A1 | 10/2002 | Mass et al. |
| 2003/0065919 | A1 | 4/2003 | Albert et al. |
| 2003/0074036 | A1 | 4/2003 | Prutchi et al. |
| 2003/0114897 | A1 | 6/2003 | Von Arx et al. |
| 2003/0114898 | A1* | 6/2003 | Von Arx et al. .............. 607/60 |
| 2003/0159048 | A1 | 8/2003 | Matsumoto et al. |
| 2004/0009815 | A1 | 1/2004 | Zotto et al. |
| 2004/0030260 | A1 | 2/2004 | Von Arx |
| 2004/0122489 | A1 | 6/2004 | Mazar et al. |
| 2004/0168071 | A1 | 8/2004 | Silverbrook |
| 2004/0260363 | A1 | 12/2004 | Arx et al. |
| 2005/0203582 | A1 | 9/2005 | Healy et al. |
| 2005/0240245 | A1 | 10/2005 | Bange et al. |
| 2005/0261934 | A1 | 11/2005 | Thompson |
| 2005/0283208 | A1 | 12/2005 | Von Arx et al. |
| 2006/0030902 | A1 | 2/2006 | Quiles et al. |
| 2006/0030904 | A1 | 2/2006 | Quiles |
| 2007/0135216 | A1 | 6/2007 | Martinek et al. |
| 2007/0169181 | A1 | 7/2007 | Roskind |
| 2007/0282398 | A1 | 12/2007 | Healy et al. |
| 2008/0046745 | A1 | 2/2008 | Buch et al. |
| 2011/0066211 | A1 | 3/2011 | Von Arx et al. |
| 2011/0098788 | A1 | 4/2011 | Quiles |

FOREIGN PATENT DOCUMENTS

| | | |
|---|---|---|
| WO | WO-2005091546 A2 | 9/2005 |
| WO | WO-2005091546 A3 | 9/2005 |
| WO | WO-2006020549 A1 | 2/2006 |

OTHER PUBLICATIONS

"U.S. Appl. No. 12/648,687, Notice of Allowance mailed Aug. 17, 2010", 7 pgs.

"U.S. Appl. No. 12/950,359, Notice of Allowance mailed Jun. 23, 2011", 8 pgs.

"Japanese Application Serial No. 2006-517513, Notice of Allowance mailed Jan. 21, 2011", 3 pgs.

"Japanese Application Serial No. 2006-517513, Office Action mailed Jan. 18, 2010", (w/ English Translation), 5 pgs.

"Japanese Application Serial No. 2006-517513, Office Action mailed Oct. 12, 2010", 1 pg.

"Japanese Application Serial No. 2006-517513, Response filed Apr. 19, 2010 to Office Action mailed Jan. 18, 2010", (w/ English Translation of Amended Claims), 41 pgs.

"Japanese Application Serial No. 2006-517513, Response filed Dec. 13, 2010 to Office Action Sep. 14, 2010", (w/ English Translation of Amended Claims), 16 pgs.

Wikipedia, SHA hash functions: http://en.wikipedia.org/wiki/SHA, (1993), 8 pgs.

"U.S. Appl. No. 10/601,763, Non Final Office Action mailed Feb. 23, 2006", 9 pgs.

"U.S. Appl. No. 10/601,763, Notice of Allowance mailed Aug. 4, 2006", 8 pgs.

"U.S. Appl. No. 10/601,763, Response filed May 23, 2006 to Non Final Office Action mailed Feb. 23, 2006", 13 pgs.

"U.S. Appl. No. 10/601,763, Supplemental Notice of Allowability mailed Oct. 23, 2006", 4 pgs.

"U.S. Appl. No. 10/801,070, Amendment Under 37 CFR 1.312 filed Apr. 11, 2007", 4 pgs.

"U.S. Appl. No. 10/801,070, Non Final Office Action mailed Feb. 6, 2006", 17 pgs.

"U.S. Appl. No. 10/801,070, Non Final Office Action mailed Jun. 16, 2006", 6 pgs.

"U.S. Appl. No. 10/801,070, Non-Final Office Action mailed Feb. 6, 2006", 20 pgs.

"U.S. Appl. No. 10/801,070, Non-Final Office Action mailed Jun. 16, 2006", 6 pgs.

"U.S. Appl. No. 10/801,070, Response filed Mar. 7, 2006 to Non Final Office Action mailed Feb. 6, 2006", 10 pgs.

"U.S. Appl. No. 10/801,070, Response filed Sep. 18, 2006 to Non Final Office Action mailed Jun. 16, 2006", 11 pgs.

"U.S. Appl. No. 10/801,070, Response filed Mar. 7, 2006 to Non-Final Office Action", 14 pgs.

"U.S. Appl. No. 10/801,070, Response filed Sep. 18, 2006 to Non-Final Office Action", 15 pgs.

"U.S. Appl. No. 10/870,324, Advisory Action mailed Mar. 21, 2008", 3 pgs.

"U.S. Appl. No. 10/870,324, Final Office Action mailed Jan. 8, 2008", 8 pgs.

"U.S. Appl. No. 10/870,324, Non Final Office Action mailed Jun. 27, 2007", 6 pgs.

"U.S. Appl. No. 10/870,324, Response filed Feb. 8, 2008 to Final Office Action mailed Jan. 8, 2008", 20 pgs.

"U.S. Appl. No. 10/870,324, Response filed Oct. 29, 2007 to Non-Final Office Action mailed Jun. 27, 2007", 21 pgs.

"U.S. Appl. No. 10/914,638, Response filed Jan. 18, 2007 to Non-Final Office Action", 21 pgs.

"U.S. Appl. No. 10/914,641, Final Office Action dated Apr. 17, 2007", 10 pgs.

"U.S. Appl. No. 10/914,641, Final Office Action mailed Mar. 10, 2009", 10 pgs.

"U.S. Appl. No. 10/914,641, Final Office Action mailed Mar. 11, 2010", 11 pgs.

"U.S. Appl. No. 10/914,641, Final Office Action mailed Feb. 20, 2008", 9 pgs.

(56) References Cited

OTHER PUBLICATIONS

"U.S. Appl. No. 10/914,641, Final office action mailed Mar. 15, 2007", 10 pgs.
"U.S. Appl. No. 10/914,641, Non-Final Office Action mailed Aug. 18, 2009", 11 pgs.
"U.S. Appl. No. 10/914,641, Non-Final Office Action mailed Aug. 22, 2008", 10 pgs.
"U.S. Appl. No. 10/914,641, Non-final office action mailed Aug. 2, 2006", 9 pgs.
"U.S. Appl. No. 10/914,641, Non-Final Office Action Mailed Aug. 31, 2007", 9 pgs.
"U.S. Appl. No. 10/914,641, Notice of Allowance dated Jan. 12, 2007", 7 pgs.
"U.S. Appl. No. 10/914,641, Notice of Allowance dated Aug. 4, 2006", 8 pgs.
"U.S. Appl. No. 10/914,641, Response filed Jan. 2, 2007 Non-Final Office Action mailed Aug. 2, 2006", 9 pgs.
"U.S. Appl. No. 10/914,641, Response filed May 11, 2009 to Final Office Action mailed Mar. 10, 2009", 12 pgs.
"U.S. Appl. No. 10/914,641, Response filed May 18, 2010 to Final Office Action mailed Mar. 11, 2010", 11 pgs.
"U.S. Appl. No. 10/914,641, Response filed Jun. 10, 2009 to Advisory Action mailed Mar. 10, 2009", 11 pgs.
"U.S. Appl. No. 10/914,641, Response filed Nov. 18, 2009 to Non Final Office Action mailed Aug. 18, 2009", 11 pgs.
"U.S. Appl. No. 10/914,641, Response filed Nov. 30, 2007 to Non-Final Office Action mailed Aug. 31, 2007", 14 pgs.
"U.S. Appl. No. 10/914,641, Response filed Nov. 24, 2008 to Non-Final Office Action mailed Aug. 22, 2008", 11 pgs.
"U.S. Appl. No. 10/914,641, Response filed Jun. 16, 2006 to Restriction Requirement mailed May 16, 2006", 5 pgs.
"U.S. Appl. No. 10/914,641, Response filed Jul. 16, 2007 Final Office Action mailed Mar. 15, 2007", 9 pgs.
"U.S. Appl. No. 10/914,641, Response to Final Office Action filed Jul. 16, 2007", 9 pgs.
"U.S. Appl. No. 10/914,641, Restriction Requirement mailed May 16, 2006", 5 pgs.
"U.S. Appl. No. 11/738,942, Non-Final Office Action mailed Jan. 20, 2010", 8 pgs.
"U.S. Appl. No. 11/738,942, Non-Final Office Action mailed Jun. 9, 2009", 14 pgs.
"U.S. Appl. No. 11/738,942, Notice of Allowance mailed Jun. 17, 2010", 9 pgs.
"U.S. Appl. No. 11/738,942, Preliminary Amendment filed Apr. 23, 2007", 6 pgs.
"U.S. Appl. No. 11/738,942, Response filed Apr. 20, 2010 to Non Final Office Action mailed Jan. 20, 2010", 10 pgs.
"U.S. Appl. No. 11/738,942, Response filed Sep. 16, 2009 to Non Final Office Action mailed Jun. 9, 2009", 9 pgs.
"International Application No. PCT/US2004/019902, International Search Report dated Dec. 6, 2004", 4 pgs.
"International Application No. PCT/US2004/019902, Written Opinion dated Dec. 6, 2004", 6 pgs.
"International Application No. PCT/US2005/008521, International Preliminary Report on Patentability mailed Sep. 28, 2006", 13 pgs.
"International Application No. PCT/US2005/008521, International Search Report mailed Oct. 11, 2005", 19 pgs.
"International Application No. PCT/US2005/008521, Invitation to Pay Additional Fees and Partial International Search Report, mailed Jul. 29, 2009", 7 pgs.
"International Application No. PCT/US2005/028052, International Preliminary Report on Patentability mailed Feb. 22, 2007", 8 pgs.
"International Application No. PCT/US2005/028052, International Search Report and Written Opinion mailed Nov. 29, 2005", 12 pgs.
"International Application No. PCT/US2005/028059, International Preliminary Report on Patentability mailed Feb. 13, 2007", 9 pgs.
"International Application No. PCT/US2005/028059, International Search Report and Written Opinion mailed Jan. 12, 2005", 13 pgs.
Healy, S. J., et al., "Cryptographic Authentication for Telemetry With an Implantable Medical Device", U.S. Appl. No. 10/801,070, filed Mar. 15, 2004, 38 pgs.
Healy, S. J., et al., "System and Method for Providing Secure Exchange of Sensitive Information With an Implantable Medical Device", U.S. Appl. No. 10/801,150, filed Mar. 15, 2004, 30 pgs.
Katoozi, M., et al., "On-Demand Retransmission of Data With an Implantable Medical Device", U.S. Appl. No. 10/870,328, Application filed Jun. 17, 2004, 30 pgs.
Quiles, S., "Secure Remote Access for an Implantable Medical Device", U.S. Appl. No. 10/914,641, filed Aug. 9, 2004, 41 pgs.
Von Arx, J., et al., "System and Method for Securely Authenticating a Data Exchange Session With an Implantable Medical Device", U.S. Appl. No. 10/800,806, filed Mar. 15, 2004, 47 pgs.
"U.S. Appl. No. 11/381,493, Decision on Appeal mailed Sep. 25, 2012", 14 pgs.
"U.S. Appl. No. 12/684,303, Final Office Action mailed Mar. 4, 2013", 8 pgs.
"U.S. Appl. No. 12/684,303, Non Final Office Action mailed May 2, 2012", 6 pgs.
"U.S. Appl. No. 12/684,303, Notice of Allowance mailed May 24, 2013", 9 pgs.
"U.S. Appl. No. 12/684,303, Response filed Apr. 1, 2013 to Final Office Action mailed Mar. 4, 2013", 9 pgs.
"U.S. Appl. No. 12/684,303, Response filed Sep. 6, 2012 to Non Final Office Action mailed May 2, 2012", 8 pgs.
"U.S. Appl. No. 12/986,333, Final Office Action mailed Dec. 11, 2012", 8 pgs.
"U.S. Appl. No. 12/986,333, Non Final Office Action mailed Jun. 22, 2012", 7 pgs.
"U.S. Appl. No. 12/986,333, Notice of Allowance mailed Mar. 27, 2013", 6 pgs.
"U.S. Appl. No. 12/986,333, Response filed Jan. 9, 2013 to Final Office Action mailed Dec. 11, 2012", 8 pgs.
"U.S. Appl. No. 12/986,333, Response filed Sep. 7, 2012 to Non Final Office Action mailed Jun. 22, 2012", 9 pgs.

* cited by examiner

SECURE LONG-RANGE TELEMETRY FOR IMPLANTABLE MEDICAL DEVICE

CROSS REFERENCE TO RELATED APPLICATION(S)

This application is a continuation of U.S. patent application Ser. No. 10/601,763, filed on Jun. 23, 2003, now issued as U.S. Pat. No. 7,155,290, the specification of which is incorporated herein by reference.

FIELD OF THE INVENTION

This invention pertains to implantable medical devices such as cardiac pacemakers and implantable cardioverter/defibrillators. In particular, the invention relates to a system and method for transmitting telemetry data from such devices.

BACKGROUND

Implantable medical devices (IMDs), including cardiac rhythm management devices such as pacemakers and implantable cardioverter/defibrillators, typically have the capability to communicate data with an external device called an external programmer via a radio-frequency telemetry link. One use of such an external programmer is to program the operating parameters of an implanted medical device. For example, the pacing mode and other operating characteristics of a pacemaker are typically modified after implantation in this manner. Modern implantable devices also include the capability for bidirectional communication so that information can be transmitted to the programmer from the implanted device. Among the data that may typically be telemetered from an implantable device are various operating parameters and physiological data, the latter either collected in real-time or stored from previous monitoring operations.

External programmers are commonly configured to communicate with an IMD over an inductive link. Coil antennas in the external programmer and the IMD are inductively coupled so that data can be transmitted by modulating a radio-frequency carrier waveform which corresponds to the resonant frequency of the two coupled coils. An inductive link is a short-range communications channel requiring that the coil antenna of the external device be in close proximity to the IMD, typically within a few inches. Other types of telemetry systems may utilize far-field electromagnetic radiation or other types of data links such as telephone lines or networks (including the internet) to enable communications over greater distances. Such long-range telemetry allows the implantable device to transmit data to a remote monitoring unit or be programmed from a remote location. Long-range telemetry thus allows physicians to monitor patients and to conduct patient follow-ups from across the room or even across the world.

Long-term telemetry for implantable medical devices, however, causes some special concerns which are not present with short-range telemetry. Communication with an implantable device over a short-range communications channel such as an inductive link requires that the external device be near the patient, so that the clinician knows whose implantable device is being programmed and the patient knows who is programming and receiving data from the implantable device. Long-range telemetry, on the other hand, does not require such physical proximity and allows the possibility of a physician inadvertently programming the wrong device. Communications with far-field electromagnetic radiation or over some kind of network also allows the communications to be intercepted by an unintended user, raising privacy concerns for the patient. A malicious user might even try to use the long-range telemetry system to re-program an implanted device. The present invention is a system and method for providing long-range telemetry which addresses these concerns.

SUMMARY

The present invention relates to a method and system for enabling secure communications between an implantable medical device (IMD) and an external device (ED) over a telemetry channel. In one embodiment, a telemetry interlock is implemented which limits any communications between the ED and the IMD over the telemetry channel. The telemetry interlock is released when the ED transmits an enable command to the IMD via a short-range communications channel requiring physical proximity to the IMD. In another embodiment, a data communications session between the IMD and ED over the telemetry channel is allowed to occur only after the IMD and ED have been authenticated to one other. The IMD is authenticated to the ED when the ED receives a message from the IMD evidencing use of an encryption key expected to be possessed by the IMD, and the ED is authenticated to the IMD when the IMD receives a message from the ED evidencing use of an encryption key expected to be possessed by the ED.

DETAILED DESCRIPTION

Figure 1:
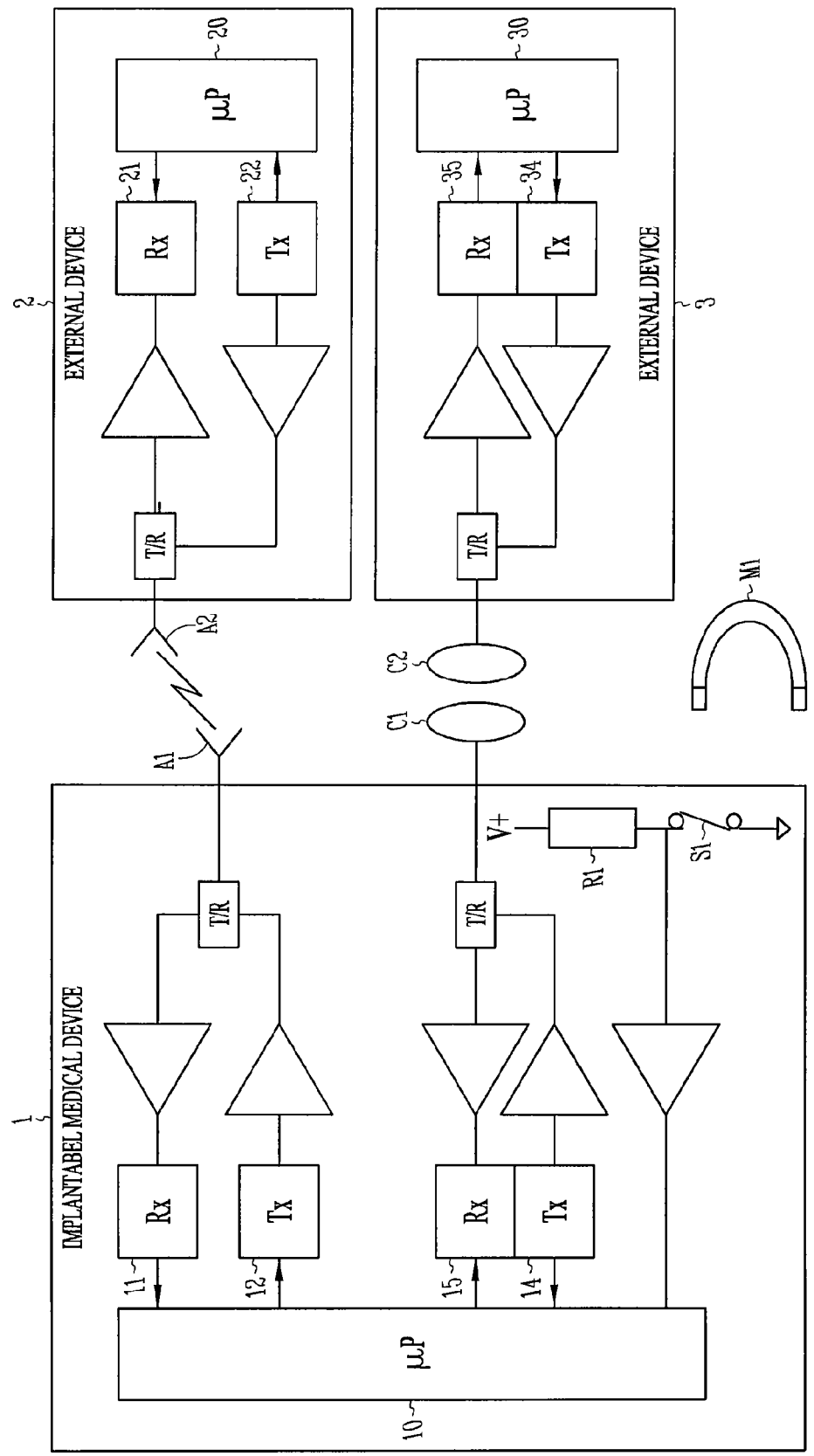
FIG. 1 is a block diagram of an exemplary telemetry system for an implantable medical device.

The present invention relates to a long-range telemetry system for implantable medical devices which guards against the possibility of malicious or inadvertent re-programming of an implanted device. In another aspect, the system may also provide for maintaining the confidentiality of data transmissions. Ensuring such patient safety and confidentiality may be accomplished using three separate techniques: encryption of data, authentication of the participants in a telemetry session, and telemetry interlock.

1. Encryption/Decryption

Encryption refers to cryptographic algorithms which are used to encode messages in such a way that they cannot be read without possession of a special key that decrypts the message. Encryption of a message is performed by applying an encryption function to the message, where the encryption function is defined by a cryptographic algorithm and an encryption key. In the following descriptions and referenced drawings, such an encrypted message will be designated as E(m,k), where E is the encryption function, m is an unencrypted message, and k is the key used to encrypt the message. Decryption of a message involves the application of a reverse function D to an encrypted message m using a decryption key k, designated as D(m,k).

The encryption and decryption keys may be the same or different depending upon the type of cryptographic algorithm which is used. In secret key cryptography, both participants in a communication share a single secret key which is used for both encryption and decryption of a message. Thus a message m encrypted by a secret key encryption function E with a key k is recovered by applying the decryption function D with same key k:

$$m=D(E(m,k),k)$$

Well-known examples of secret key cryptographic algorithms are DES (Data Encryption Standard), AES (American Encryption Standard), triple-DES, and Blowfish.

In public key cryptography, on the other hand, the encryption and decryption keys are different. In order to send a secure message using public key cryptography, the sender encrypts the message with the recipient's public key which is known to all authorized senders and may be widely-known to allow anyone to send a message. The message can then only be decrypted by the private key which corresponds to the public key used to encrypt the message, the private key being held by the message recipient and shared with no one else. Thus, a message encrypted with a public key encryption function E with a public key k1 is recovered by applying the decryption function D with the corresponding private key k2:

$$m=D(E(m,k1),k2)$$

Each participant in a secure two-way communications session must therefore possess its own private key and know the other's public key. A well-known example of a public key cryptographic algorithm is RSA.

Although either public key or secret key cryptography may be used to securely transmit data, public key cryptographic algorithms are much more computationally intensive. For this reason, it would usually be preferable to use secret key cryptography for the actual data communications between an implantable device and an external device. As explained below, however, public key cryptography may be advantageously used for authentication and to transmit the secret keys used for the data communications.

2. Authentication

Authentication refers to the mechanisms or protocols by which the participants in a communications session may reliably identify one another. An authentication protocol may be implemented using either secret key or public key cryptography to allow an implantable medical device (IMD) and an external device (ED) to authenticate one another. A data communications session between the IMD and ED over the telemetry channel is allowed to occur only after the IMD and ED have been authenticated to one other. With authentication by either public key or secret key cryptography, the IMD is authenticated to the ED when the ED receives a message from the IMD evidencing use of an encryption key expected to be possessed by the IMD, and the ED is authenticated to the IMD when the IMD receives a message from the ED evidencing use of an encryption key expected to be possessed by the ED.

In authentication by secret key cryptography, the IMD is authenticated to the ED when the ED transmits a first message to the IMD over the telemetry channel and receives in response a message derived from the first message which is encrypted by a secret key expected to be possessed by the IMD. The ED is then authenticated to the IMD when the IMD transmits a second message to the ED over the telemetry channel and receives in response a message derived from the second message which is encrypted by a secret key expected to be possessed by the ED.

An authentication protocol employing public key cryptography would work as follows. The IMD is authenticated to the ED when the ED encrypts a first message with a public key having a corresponding private key expected to be possessed by the IMD, transmits the encrypted first message over the telemetry channel to the IMD, and receives in response a message from the IMD derived from the first message which evidences possession of the corresponding private key by the IMD. The ED is authenticated to the IMD when the IMD encrypts a second message with a public key having a corresponding private key expected to be possessed by the ED, transmits the encrypted second message over the telemetry channel to the ED, and receives in response a message from the ED derived from the second message which evidences possession of the corresponding private key by the ED. The messages derived from the first and second messages may include the first and second messages, respectively, along with identifying data such as identity codes for the ED and IMD. Rather than having separate transmissions for each, the IMD may transmit the message derived from the first message and the second message as a combined message (i.e., the message derived from the first message which is transmitted by the IMD would then include the second message). In one embodiment, the first and second messages include random numbers generated by the ED and IMD, respectively. The messages derived from the first and second messages would then either include the respective random number itself or a number derived therefrom (e.g., the random number incremented by one). In order to maintain confidentiality of the responses which authenticate one participant to the other, the messages derived from the first and second messages and which are transmitted by the IMD and ED, respectively, may be encrypted using the public keys of the ED and IMD, respectively.

3. Telemetry Interlock

As explained above, cryptographic techniques may be used both to authenticate the IMD and ED to one another and to securely transmit data. All cryptographic techniques, however, depend upon either the secret key or private key being kept secret. In order to give the patient added security with respect to long-range telemetry, a technique referred to herein as a telemetry interlock is employed. A telemetry interlock is a technique which limits any communications between the ED and the IMD over the long-range telemetry link until the interlock is released. The telemetry interlock is released by transmitting an enable command to the IMD via a short-range communications channel requiring physical proximity to the IMD. In one embodiment, no information at all is allowed to be transmitted until the interlock is released. This is the more secure embodiment. In a second embodiment limited information is allowed, but programming of the device is not. This embodiment supports remote patient monitoring without the patient having to release the interlock.

One way of implementing the telemetry interlock is to use an inductive link as the short-range communications channel. As noted above, traditional implantable medical devices have an inductive telemetry link that is very short range just a few inches). In this implementation of a telemetry interlock, the IMD hardware will require that an inductive link be established with keys exchanged inductively to release the long-range telemetry interlock. In one embodiment the release of the telemetry interlock would time out after a few tens of minutes, and again a wave of the inductive wand over the device would be needed to continue the session. In another embodiment the telemetry interlock would not expire until the end of the current telemetry session.

Another way of implementing the telemetry interlock is to use the static magnetic field of a magnet as a short-range communications channel so that the telemetry interlock is released when a magnet is held near the IMD. This embodiment may be needed in cases where the IMD is not equipped with an inductive telemetry system. The doctor or other person trusted by the patient would then be required to wave a magnet over the implantable medical device to enable programming. Again the release of the interlock would expire after either some short duration of time or at the end of the present telemetry session.

Both of these interlock techniques will stop malicious programming from a remote hacker because the interlock can only be released by someone physically very close to the patient. These interlock techniques will also stop unintentional programming by a valid user. Because a doctor or other authorized user may accidentally establish a telemetry session with the wrong device (long range telemetry will allow multiple patients to be in range of a doctor's programmer), having to wave an inductive wand or magnet over the device to enable programming would prevent the doctor from accidentally programming the wrong device.

4. Secure Data Communications Session

Once authentication and release of the telemetry interlock have occurred, the IMD and the ED can proceed to communicate data over the long-range telemetry link with each device knowing that the other is not an impostor. If the data is sent in the clear during the data communications session, however, an eavesdropper could intercept the data and compromise the patient's privacy. It may therefore be desirable to encrypt some or all communications between the ED and the IMD during the data communications session. As stated earlier, secret key encryption is much less computationally intensive than public key encryption and is preferred for transmitting relatively large amounts of data. If secret key cryptography is used for authentication, the ED and IMD can use the same secret key for data transmission. If public key cryptography is used for authentication, secret key cryptography can be used for data communications, where one of either the ED or the IMD transmits to the other of either the ED or the IMD a secret session key encrypted by the latter's public key. That secret session key can then be used by both participants to encrypt data.

5. Exemplary Hardware Description

FIG. 1 is a block diagram of the telemetry components of an implantable medical device 1 and two representative external devices 2 and 3. Each of the devices has a microprocessor or other type of controller designated 10, 20, or 30 for processing the digital data. Software or firmware executed by the controller in each device may implement various communications algorithms and protocols when transmitting or receiving messages, including the encryption, authentication, and telemetry interlock schemes described above. A data receiver and a data transmitter are interfaced to the controller in each of the devices for receiving and transmitting either a modulated carrier signal or a baseband signal. A demodulator or decoder for extracting digital data from the carrier signal or baseband signal is incorporated into each receiver. A modulator or encoder is incorporated into each transmitter for modulating the carrier signal with digital data or encoding the baseband signal. The data transmitted by each of the devices is digital data that can be transmitted directly as baseband data in certain types of data links or as a modulated carrier signal. In either case, the data is transmitted in the form of symbols representing one or more bits of information. For example, in on-off amplitude shift keying, each pulse represents either a one or a zero. Other modulation methods (e.g., M-ary modulation techniques) utilize symbols representing a greater number of bits.

Each of the external devices 2 and 3 would typically be an external programmer which can both re-program and download data from the implantable device 1. The external device 3 is intended to represent a device designed for short-range telemetry via an inductive link where a coil C3 is interfaced to the receiver 35 and transmitter 34 for inductively linking with a corresponding coil C1 interfaced to the receiver 15 and transmitter 14 of the implantable device. The coil C3 would typically be incorporated into a wand for positioning close to the implantable device, while the coil C1 is typically wrapped around the periphery of the inside of the implantable device casing. An example of an inductive link telemetry system for an external programmer and a cardiac pacemaker is described in U.S. Pat. No. 4,562,841, issued to Brockway et al. and assigned to Cardiac Pacemakers, Inc., the disclosure of which is hereby incorporated by reference. The external device 2 is intended to depict a device which communicates with the implantable device 1 over a long-range telemetry link, implemented with either far-field radio transmissions or over a network. For transmitting and receiving data between the devices over the long-range telemetry link, a data receiver 11 and a data transmitter 12 are interfaced to the controller in the implantable device 1, and a data receiver 21 and a data transmitter 22 are interfaced to the controller in the external device 2. In the case of a far-field radio link, the receiver/transmitter pair of the implantable device 1 and external device 2 are interfaced to antennas A1 and A2, respectively. In the case where long-range telemetry is implemented over a network, the receiver/transmitter pair of external device 2 would be interfaced to a network connection, while the implantable device would 1 would be wirelessly interfaced to a repeater unit with a network connection.

The implantable device 1 is also equipped with a magnetically actuated switch S1 and associated pull-up resistor R1 which is interfaced to the controller 10. In this embodiment, the telemetry interlock may be released by either a command transmitted from the external device 3 over the inductive link formed by the coils C1 and C3 or by actuation of the switch S1 by proximity of an external magnet M1 may be used to release the telemetry interlock. In other embodiments, the implantable device would perhaps only have one type of short-range communications channel for releasing the telemetry interlock, either a magnetically actuated switch or an inductive link telemetry system. Other types of short-range communications channels for releasing the telemetry interlock are also possible, including short-range telemetry systems implemented with a capacitive link or a physically actuated switch.

6. Exemplary Specific Embodiments

As described above, a system in accordance with the invention for providing secure long-range telemetry for an implantable medical device may include any one or all of the following: 1) a telemetry interlock released via a short-range communications channel, 2) an authentication protocol by which an external device and the implantable device can identify one other, and 3) encryption of the long-range telemetry communications to ensure patient privacy. The following are descriptions of exemplary schemes which incorporate those features.

In one particular embodiment, the telemetry interlock technique described above is used as the sole means for providing security before the initiation of a long-range telemetry session, with no cryptographic authentication protocols being employed and the data sent in the clear. In another embodiment, only cryptographic authentication is used to provide security for initiating a long-range telemetry session, with no use of a telemetry interlock. In either of these embodiments, a long-range telemetry session can either be prevented entirely or limited to particular types of data transfers if no release of the telemetry interlock or cryptographic authentication occurs. For example, while it would probably not be desirable to allow an external device to program an implantable device via long-range telemetry without either release of a telemetry interlock or cryptographic authentication, certain types of data could still be allowed to be transferred from the implantable device, either with or without encryption. In another embodiment, neither cryptographic authentication nor a telemetry interlock is employed, but the implantable device uses either public key or secret key encryption to send certain types of data to an external device over a long-range telemetry link.

One example embodiment of a method or system for enabling secure communications between an implantable medical device (IMD) and an external device (ED) over a telemetry channel includes a telemetry interlock which limits any communications between the ED and the IMD over the telemetry channel, where the telemetry interlock is released by transmitting an enable command to the IMD via a short-range communications channel requiring physical proximity to the IMD. The IMD is authenticated to the ED when the ED receives a message from the IMD evidencing use of an encryption key expected to be possessed by the IMD, and the ED is authenticated to the IMD when the IMD receives a message from the ED evidencing use of an encryption key expected to be possessed by the ED. A data communications session between the IMD and ED over the telemetry channel is then allowed to occur only after the IMD and ED have been authenticated to one other. Either public key or secret key cryptography can be used for the authentication. In another example embodiment, secure communications between IMD and an ED over a telemetry channel is provided solely by a telemetry interlock which is released by transmitting an enable command to the IMD via a short-range communications channel requiring physical proximity to the IMD, where data communications between the IMD and ED over the telemetry channel is limited until the telemetry interlock has been released.

In another example embodiment, secure communications between an IMD and an ED over a telemetry channel is provided by authenticating the IMD to the ED when the ED receives a message from the IMD evidencing use of an encryption key expected to be possessed by the IMD, authenticating the ED to the IMD when the IMD receives a message from the ED evidencing use of an encryption key expected to be possessed by the ED, and allowing a data communications session between the IMD and ED over the telemetry channel to occur only after the IMD has been authenticated to the ED. In another embodiment, unilateral authentication is employed so that only one of either the IMD or the ED needs to be authenticated to the other before a data communications session is allowed to occur. For example, when an ED communicates with an IMD, it may authenticate the IMD so that the ED knows that it is gathering data from the correct device. However, the IMD may not need to authenticate the ED unless the ED tries to alter its state (re-program it). As long as the ED is only reading data, there is no safety concern (although there may be a privacy concern).

Figure 2:
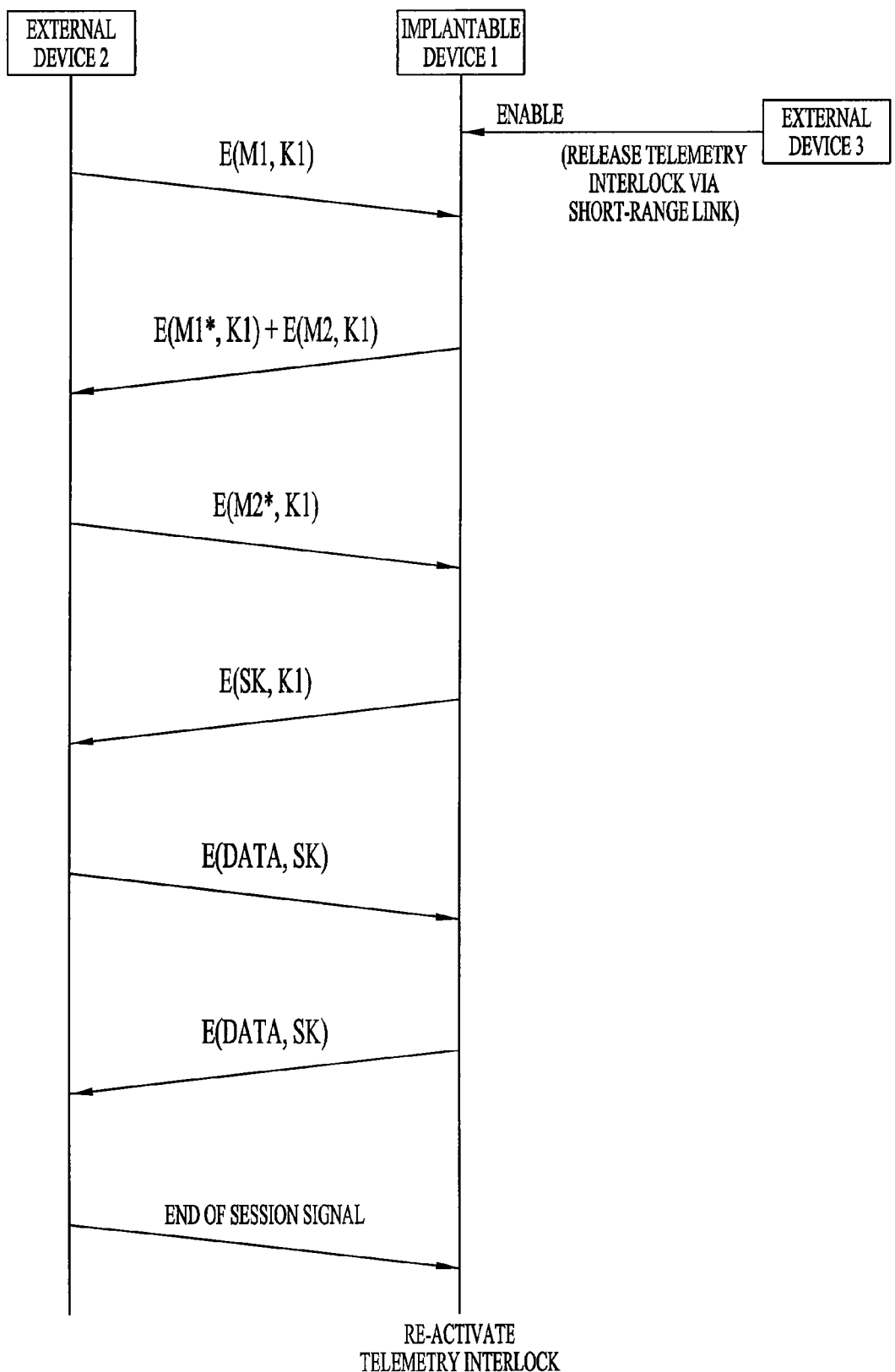
FIG. 2 illustrates a secret key authentication protocol.

FIG. 2 depicts a communications session between the external device 2 and the implantable device 1 over a long-range telemetry channel in an embodiment using a telemetry interlock and where authentication is performed with secret key cryptography. After the telemetry lock is released by an ENABLE command from the external device 3, the external device 2 transmits a message M1 encrypted by a secret key encryption algorithm using a key K1. The implantable device 1 responds by decrypting the message to obtain M1, modifying M1 in an agreed upon manner (e.g., incrementing the number M1 by one) to obtain M1*, transmitting M1* back to the implantable device encrypted by the key K1. After decrypting the message to obtain M1*, the external device 2 has authenticated the implantable device 1, as the latter has evidenced possession of the secret key K1. The implantable device 1 at the same time sends a message M2 encrypted by secret key K1. The external device 2 responds by decrypting the message to obtain M2, modifying M2 to obtain M2*, and transmitting M2* encrypted with key K1 back to the implantable device 1, thus authenticating the external device 2. The implantable device 1 then transmits a secret session key SK encrypted by key K1. A data communications session may then ensue in which DATA is transmitted by either of the devices encrypted with the secret session key SK. In another embodiment, data is exchanged between the devices during the data communications session using the same secret key K1 as used for authentication. The session continues until one of the devices sends an end of session signal or a time-out occurs, at which point the telemetry interlock is re-activated.

Figure 3:
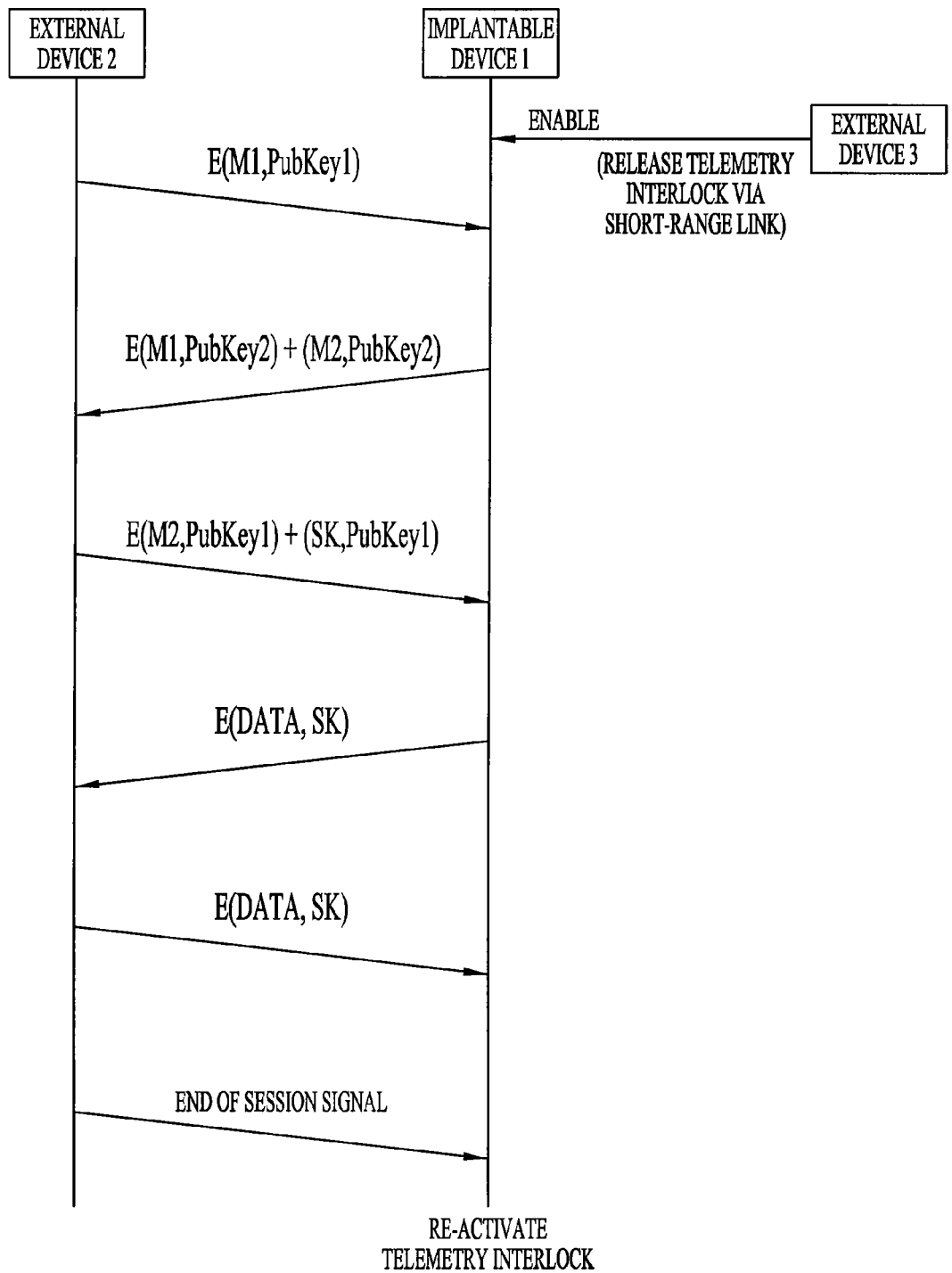
FIG. 3 illustrates a public key authentication protocol.

FIG. 3 depicts a communications session between the external device 2 and the implantable device 1 over a long-range telemetry channel in an embodiment using a telemetry interlock and where authentication is performed with public key cryptography. After the telemetry lock is released by an ENABLE command from the external device 3, the external device 2 transmits a message M1 encrypted by a public key encryption algorithm using a key PubKey1 having a corresponding private key thought to be possessed by the implantable device. The implantable device responds by decrypting the message with the private key corresponding to PubKey1 to obtain M1 and transmitting M1 back to the implantable device encrypted by a public key PubKey2 having a corresponding private key thought to be possessed by the external device 2. When the external device 2 decrypts the message with its private key and obtains M1, the external device 2 has authenticated the implantable device 1, as the latter has evidenced possession of the private key corresponding to public key PubKey1. The implantable device 1 at the same time sends a message M2 also encrypted by public key PubKey2. The external device 2 responds by decrypting the message with the private key corresponding to public key PubKey2 to obtain M2 and transmitting M2 encrypted with public key PubKey1 back to the implantable device 1, thus authenticating the external device 2 to the implantable device. The external device 2 also transmits a secret session key SK encrypted by encrypted with public key PubKey1. A data communications session may then ensue using secret key cryptography in which DATA is transmitted by either of the devices encrypted with the secret session key SK. The session continues until one of the devices sends an end of session signal or a time-out occurs, at which point the telemetry interlock is re-activated.

Figure 4:
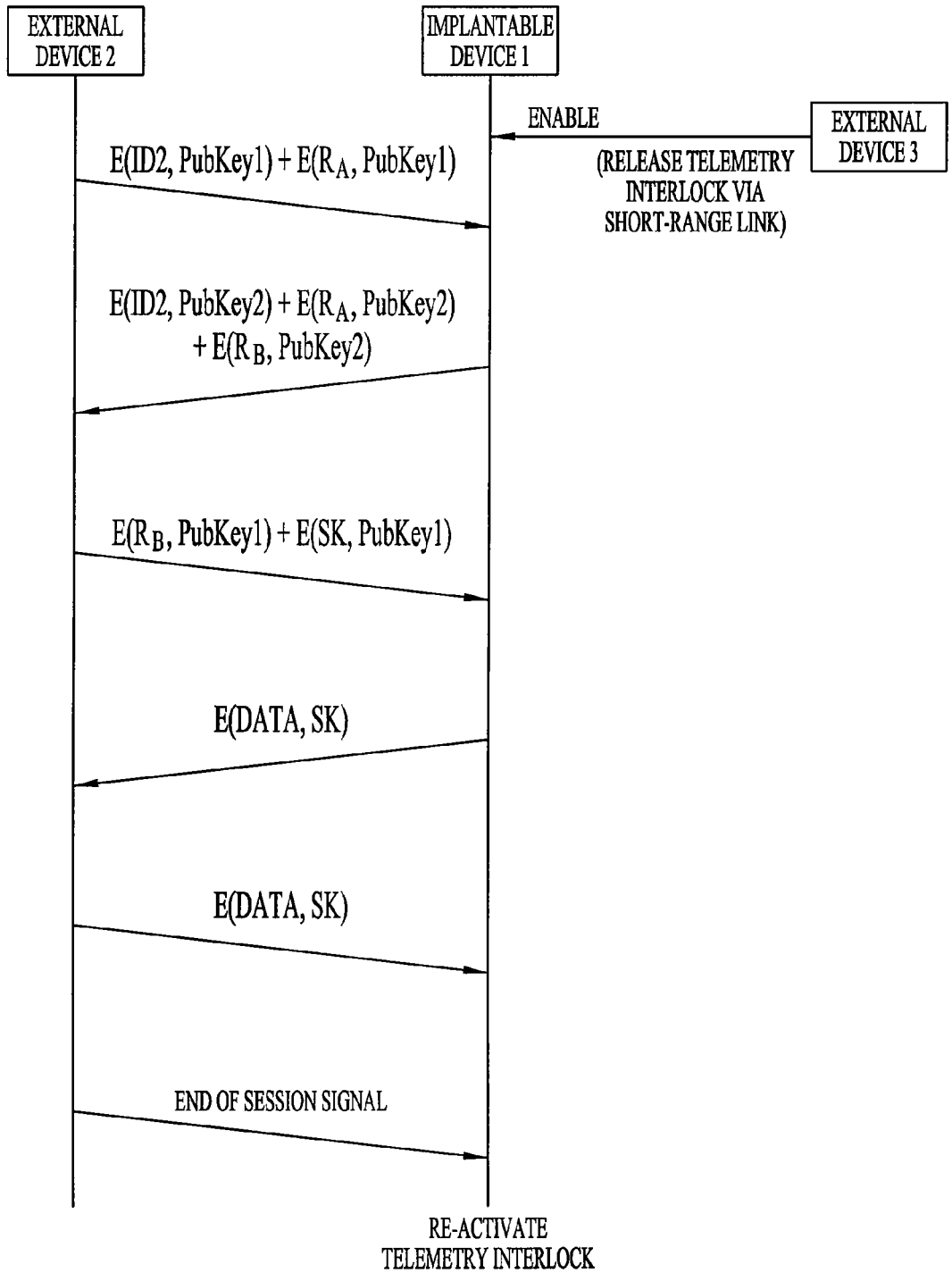
FIG. 4 illustrates a particular public key authentication protocol.

FIG. 4 depicts a communications session using a more specific embodiment of the authentication protocol illustrated in FIG. 3. It is assumed that the external device 2 and the implantable device know each other's public authentication key. When an instigator (in this embodiment, the instigator is the external device 2) wants to establish an authenticated long-range telemetry session with an implantable device, it begins by encrypting its identity ID2 and a random number RA with the implantable device's public key PubKey1. No listener except the intended recipient will be able to decrypt this information (even if the listener knows the recipient's public key) because no one except the intended recipient knows the recipient's private key. The recipient device decrypts this message with its private key. It then looks up the public key of the instigator PubKey2 and uses this to encrypt its identity ID1, the random number $R_A$, and a second random number $R_B$. The recipient then transmits this encrypted information back to the instigator. Again, no one but the instigator is able to decrypt this information because no one but the instigator knows the instigator's private key. The instigator upon receiving back and verifying the random number it sent $R_A$, now knows that the implantable device it is communicating with is in fact the intended device, because only the intended device could have decrypted and returned $R_A$. The instigator then encrypts $R_B$ with the recipient's public key PubKey1 and sends this back to the recipient. Upon receiving, decrypting, and verifying $R_B$, the recipient now knows that the instigator is in fact the holder of the correct private key, because only the holder of that private key could have decrypted and returned $R_B$. Authentication has now occurred. Both sides of the communication session now know that its communication partner holds the proper private key. Note that in this embodiment, recording the authentication exchanges and retransmitting parts of the exchanges in an attempt to impersonate an authorized device would not work because random numbers were used by both participants in the authentication, and these will be different each time.

Again, because a public key cryptographic algorithm is computationally expensive, it is only used in the embodiment of FIG. 4 for authentication at the start of each session, and the messages encrypted are of minimal size (typically a few hundred bits). The instigator transmits a secret session key SK encrypted with public key PubKey1 so that data communications session may be performed using secret key cryptography. In this embodiment, the secret session key SK is transmitted to the recipient device during authentication in the same frame that sends back $R_B$. In this way the number of frames using public key encryption is reduced by one (and public key encryption is very computationally expensive). In a particular embodiment, the secret session key SK is 64 bits. Although a 64-bit key is easier to decipher than the 128 bit public key, it is sufficient to provide security for the relative short duration of a typical telemetry session. The data communications session continues until one of the devices sends an end of session signal or a time-out occurs, at which point the telemetry interlock is re-activated. In another particular embodiment, the session key expires at the end of each telemetry session, and a new key is chosen at random for the next session.

Even using secret key cryptography for data communications, it still may not be feasible for an implantable medical device to encrypt or decrypt every message that it sends or receives. It is not easy for the present generation of cardiac rhythm management devices to encrypt real-time electrograms without adding significant latency to the transmission. In one embodiment, therefore, the implantable medical device only encrypts selective data and sends other data in the clear. For example, only the most sensitive patient data (such as patient name, social security number and diagnosis) may be encrypted. An encryption flag in the header of each data packet could indicate if the contents are encrypted or not.

With either public key or secret key authentication, it is evidence of possession of a particular key which authenticates a device. In general, all authentication protocols are only as secure as the private keys in the case of public key cryptography and the secret keys in the case of secret key cryptography. For this reason the private or secret keys should be long (e.g., 128 bit in one embodiment). For added security, the private or secret key may be either hardwired into a device at the factory or generated internally by the device, and then prevented from being read out by telemetry. For example, a private key may be programmed into a device during manufacture, with its corresponding public key then included with the product documentation or obtainable through short-range inductive telemetry. A physician can then program the device's public key into a home monitor, a portable repeater, or a programmer. All external devices have unique public and private authentication keys as well, with the public key included with the product documentation. A physician can thus program a number of external device's public keys into an implantable device. In another embodiment, both implantable and external devices are capable of randomly generating new public/private key pairs by the RSA algorithm or through some other standard key pair generating algorithm. In this embodiment, new keys can be generated when the physician commands it via secure short-range inductive telemetry.

In a preferred embodiment, the authentication schemes described above only apply to the long-range telemetry link so that communication is always available in an emergency via short-range telemetry. For example, in case of a device reset, or some other fault that may cause the authentication keys to be corrupted, a long-range authenticated telemetry session will not be possible. In this case, short-range telemetry should still be available to reset the authentication keys. Another example of why short-range telemetry should be available without authentication is the traveling patient who needs device interrogation when away from his home physician.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for implementing communications between an implantable medical device (IMD) and an external device (ED) over a telemetry channel, comprising:
    limiting data communications between the IMD and ED over a long range telemetry channel not requiring physical proximity to the IMD until a telemetry interlock has been released, wherein the telemetry interlock is released when the IMD receives an enable command via a short-range communications channel requiring physical proximity to the IMD;
    authenticating the long range telemetry channel by transmitting a first encrypted communication from the IMD via the long range telemetry channel and receiving a second encrypted communication with the IMD via the long range telemetry channel, wherein the second message evidences that the sending device encrypted the second message using an expected encryption key; and
    allowing data communications over the long range telemetry channel between the IMD and the ED but preventing programming of the IMD over the long range telemetry channel until the telemetry interlock is released and the long range telemetry channel is authenticated.

2. The method of claim 1 wherein, after a communications session over the telemetry channel ends, the telemetry interlock is re-activated to limit communications over the telemetry channel until the telemetry interlock is again released.

3. The method of claim 1 wherein the release of the telemetry interlock times out after a specified time period at which point the telemetry interlock is re-activated.

4. The method of claim 1 wherein the short-range communications channel is an inductive communications link between the IMD and another device in proximity to the IMD.

5. The method of claim 4 wherein the IMD and the device in proximity to the IMD must exchange keys inductively before the telemetry interlock is released.

6. The method of claim 1 wherein the short-range communications channel is a switch within the IMD which is actuated by a magnet held in close proximity to the IMD to thereby release the telemetry interlock.

7. The method of claim 1 wherein the short-range communications channel is a capacitive communications link between the IMD and another device in proximity to the IMD.

8. The method of claim 1 further comprising:
authenticating the ED to the IMD when the IMD receives the second message from the ED evidencing use of an encryption key expected to be possessed by the ED; and,
limiting communications between the IMD and the ED such that a programming session over the telemetry channel cannot be established unless the ED has been authenticated to the IMD.

9. The method of claim 8 further comprising:
authenticating the IMD to the ED when the ED receives a message from the IMD evidencing use of an encryption key expected to be possessed by the IMD; and,
allowing a programming session between the IMD and ED over the telemetry channel to occur only after the IMD and ED have been authenticated to one other.

10. The method of claim 9 wherein the ED and the IMD are authenticated to one another using public key cryptography by:
authenticating the IMD to the ED when the ED encrypts a first message with a public key having a corresponding private key expected to be possessed by the IMD, transmits the encrypted first message over the telemetry channel to the IMD, and receives in response a message from the IMD derived from the first message which thereby evidences possession of the corresponding private key by the IMD; and,
authenticating the ED to the IMD when the IMD encrypts a second message with a public key having a corresponding private key expected to be possessed by the ED, transmits the encrypted second message over the telemetry channel to the ED, and receives in response a message from the ED derived from the second message which thereby evidences possession of the corresponding private key by the ED.

11. The method of claim 9 wherein the ED and the IMD are authenticated to one another using secret key cryptography by:
authenticating the IMD to the ED when the ED transmits a first message to the IMD over the telemetry channel and receives in response a message derived from the first message which is encrypted by a secret key expected to be possessed by the IMD;
authenticating the ED to the IMD when the IMD transmits a second message to the ED over the telemetry channel and receives in response a message derived from the second message which is encrypted by a secret key expected to be possessed by the ED.

12. A system for implementing communications between an implantable medical device (IMD) and an external device (ED) over a telemetry channel, comprising:
means for limiting data communications between the IMD and ED over a long range telemetry channel not requiring physical proximity to the IMD until a telemetry interlock has been released, wherein the telemetry interlock is released when the IMD receives an enable command via a short-range communications channel requiring physical proximity to the IMD;
means for authenticating the long range telemetry channel by transmitting a first encrypted communication from the IMD via the long range telemetry channel and receiving a second encrypted communication with the IMD via the long range telemetry channel, wherein the second message evidences that the sending device encrypted the second message using an expected encryption key; and
means for allowing data communications over the long range telemetry channel between the IMD and the ED but preventing programming of the IMD over the long range telemetry channel until the telemetry interlock is released and the long range telemetry channel is authenticated.

13. The system of claim 12 further comprising means for, after a communications session over the telemetry channel ends, re-activating the telemetry interlock to limit communications over the telemetry channel until the telemetry interlock is again released.

14. The system of claim 12 further comprising means for timing out the telemetry interlock after a specified time period at which point the telemetry interlock is re-activated.

15. The system of claim 12 wherein the short-range communications channel is an inductive communications link between the IMD and another device in proximity to the IMD.

16. The system of claim 15 further comprising means for preventing release of the telemetry interlock unless the IMD and the device in proximity to the IMD exchange keys inductively.

17. The system of claim 12 wherein the short-range communications channel is a switch within the IMD which is actuated by a magnet held in close proximity to the IMD to thereby release the telemetry interlock.

18. The system of claim 12 wherein the short-range communications channel is a capacitive communications link between the IMD and another device in proximity to the IMD.

19. The system of claim 12 further comprising:
means for authenticating the ED to the IMD when the IMD receives the second message from the ED evidencing use of an encryption key expected to be possessed by the ED; and,
means for limiting communications between the IMD and the ED such that a programming session over the telemetry channel cannot be established unless the ED has been authenticated to the IMD.

20. The system of claim 19 further comprising:
means for authenticating the IMD to the ED when the ED receives a message from the IMD evidencing use of an encryption key expected to be possessed by the IMD; and,
means for allowing a programming session between the IMD and ED over the telemetry channel to occur only after the IMD and ED have been authenticated to one other.

* * * * *